(12) United States Patent
Overes

(10) Patent No.: US 10,441,335 B2
(45) Date of Patent: Oct. 15, 2019

(54) BONE SCREW ASSEMBLY

(71) Applicant: IGNITE-concepts GmbH, Langendorf (CH)

(72) Inventor: Tom Overes, Langendorf (CH)

(73) Assignee: IGNITE-CONCEPTS GMBH, Langendorf (CH)

(*) Notice: Subject to any disclaimer, the term of this patent is extended or adjusted under 35 U.S.C. 154(b) by 162 days.

(21) Appl. No.: 15/117,318

(22) PCT Filed: Apr. 17, 2014

(86) PCT No.: PCT/CH2014/000052
§ 371 (c)(1),
(2) Date: Aug. 8, 2016

(87) PCT Pub. No.: WO2015/117250
PCT Pub. Date: Aug. 13, 2015

(65) Prior Publication Data
US 2016/0346024 A1    Dec. 1, 2016

(30) Foreign Application Priority Data

Feb. 6, 2014    (CH) .......................................... 154/14

(51) Int. Cl.
*A61B 17/86*    (2006.01)
*A61B 17/74*    (2006.01)

(52) U.S. Cl.
CPC .......... *A61B 17/8685* (2013.01); *A61B 17/74* (2013.01); *A61B 17/744* (2013.01); *A61B 17/746* (2013.01)

(58) Field of Classification Search
CPC ..... A61B 17/74; A61B 17/744; A61B 17/746; A61B 17/863; A61B 17/864;
(Continued)

(56) References Cited

U.S. PATENT DOCUMENTS

| 4,456,005 A * | 6/1984 | Lichty ................ A61B 17/8685 |
| | | 606/315 |
| 4,760,843 A * | 8/1988 | Fischer ................ A61B 17/686 |
| | | 411/178 |

(Continued)

FOREIGN PATENT DOCUMENTS

| WO | 2006124987 A1 | 11/2006 |
| WO | 2013071701 A1 | 5/2013 |

*Primary Examiner* — Jacqueline T Johanas
(74) *Attorney, Agent, or Firm* — MU P.C.

(57) ABSTRACT

The application relates to a bone screw assembly for fixation into a bone, comprising a first screw element with a body including a threaded first end with a first external screw thread having a first handedness and a first lead length. The first screw element comprises an internal thread feature with a second handedness and a second lead length located within a bore within said body. The screw assembly includes a second screw element comprising a second external screw thread with the second handedness and the second lead length. Said second screw element is arranged within said bore and said second external screw thread is engaged with said internal thread feature. The second screw element is movable from a first implantation configuration where the second screw element is arranged completely within said bore and a second implantation configuration where the second screw element protrudes from said bore.

14 Claims, 13 Drawing Sheets

(58) Field of Classification Search
CPC ...... A61B 17/8685; F16B 39/02; F16B 39/28; F16B 39/30; F16B 37/122
See application file for complete search history.

(56) References Cited

U.S. PATENT DOCUMENTS

| | | | | |
|---|---|---|---|---|
| 6,668,688 B2* | 12/2003 | Zhao | ................ | A61B 17/8685 411/51 |
| 8,403,973 B2* | 3/2013 | Biyani | ............... | A61B 17/8685 606/309 |
| 8,556,949 B2* | 10/2013 | Teisen | .................... | A61B 17/68 606/323 |
| 9,033,984 B2* | 5/2015 | Overes | ............... | A61B 17/7241 606/64 |
| 2003/0000350 A1* | 1/2003 | Zhao | ................ | A61B 17/8685 81/439 |
| 2003/0004514 A1 | 1/2003 | Frigg et al. | | |
| 2004/0122431 A1* | 6/2004 | Biedermann | ........ | A61B 17/864 606/62 |
| 2004/0210227 A1* | 10/2004 | Trail | .................... | A61B 17/863 606/916 |
| 2006/0155281 A1* | 7/2006 | Kaup | ................ | A61B 17/7258 606/65 |
| 2007/0014649 A1* | 1/2007 | James | ................ | A61B 17/863 411/81 |
| 2007/0213732 A1* | 9/2007 | Khanna | ............. | A61B 17/8685 606/86 A |
| 2007/0250064 A1* | 10/2007 | Darois | ................ | A61B 17/064 606/284 |
| 2008/0183220 A1* | 7/2008 | Glazer | ................ | A61B 17/686 606/303 |
| 2009/0292292 A1* | 11/2009 | Fencl | ................ | A61B 17/1659 606/104 |
| 2009/0326533 A1 | 12/2009 | Dell'Oca | | |
| 2010/0217329 A1* | 8/2010 | Brown | ................ | A61B 17/742 606/301 |
| 2010/0249852 A1* | 9/2010 | Brumfield | ............ | A61B 17/742 606/282 |
| 2011/0076640 A1* | 3/2011 | Jones | ................ | A61B 17/3472 433/89 |
| 2011/0166602 A1* | 7/2011 | Malek | ................. | A61B 17/686 606/279 |
| 2012/0095515 A1* | 4/2012 | Hamilton | ............ | A61B 17/864 606/304 |
| 2013/0053902 A1* | 2/2013 | Trudeau | ................ | A61B 17/68 606/313 |
| 2013/0338722 A1* | 12/2013 | Yalizis | ................... | A61B 17/68 606/312 |
| 2014/0066991 A1* | 3/2014 | Marik | ............... | A61B 17/7032 606/279 |
| 2014/0214034 A1* | 7/2014 | Rayes | ............... | A61B 17/8685 606/65 |
| 2015/0150615 A1* | 6/2015 | Anapliotis | ......... | A61B 17/8685 606/305 |

* cited by examiner

BONE SCREW ASSEMBLY

TECHNICAL FIELD

The present invention relates to a bone screw assembly which withstands rotational moments.

BACKGROUND ART

Various bone screws are known in the field. For the stabilisation of a bone fragment multiple screws are normally used to fix the bone fragment to a bone. If only one screw is inserted, the bone fragment could rotate around the axis of the screw and would therefore not exhibit the necessary stability. However, in many indications only one screw may be placed into the bone fragment. For example, in femoral head fractures, only one screw may be used to fixate the femoral head to the femoral shaft. However, when using a single screw, there is a risk that the femoral head rotates around the screw axis, thereby losing the fracture reduction.

Hip fractures are a common injury. The number of annual hip fractures is increasing worldwide. Especially the elderly population suffers from hip fractures. Due to the increasing number of elderly people, the annual number of hip-fractures is increasing fast. One reason for a hip fracturing is osteoporosis. With rising age, the bones become more brittle and easily fracture after a fall.

There are many types of hip-fractures, which need an individual treatment. For example a femoral neck fracture in a patient with bad cartilage on the joint surfaces is preferably treated with a total hip implant, completely replacing the joint. Fractures in patients with good quality cartilage and younger patients preferably are treated with methods that do not replace the entire joint.

Several methods of treatment are available depending on the location of the fracture, the number of bone fragments, the quality of the bone, and the size of the bone. Treatment methods vary from the insertion of two or more cannulated screws to the insertion of intramedullary nails to stabilize the bone fragments.

Another common method is the implantation of the dynamic hip screw, or sliding screw fixation. The dynamic hip screw consists of a plate which is fixated to the lateral cortex of the femoral bone, and a large screw extending from the plate into the femoral head. The screw can telescope into the plate, a so-called dynamic fixation. The dynamic fixation allows the femoral head to set itself against the femoral shaft, and the implant to shorten accordingly.

A disadvantage of the dynamic hip screw is that the screw may withstand tensile loads and compression loads, but cannot withstand torsional moments. If a rotation occurs, the fracture reduction is lost. Further, the rotation may also disrupt the blood supply to the head of the femur and cause so-called avascular necrosis. The head fragment is thereby cut off the necessary blood supply to heal. In case of avascular necrosis, in a next surgical intervention the implant is removed and replaced by a total hip prosthesis.

Often an extra anti-rotation screw is placed above the dynamic hip screw implant to overcome this problem. The disadvantage of the additional screw is that the necessary bone stock must be available and the telescoping of the screw into the plate might be compromised. Especially in small stature patients the femoral neck may simply be too small for the application of an extra anti-rotation screw.

Other available designs to secure the implant from torsional moments comprise two parallel screws extending into the femoral head, wherein both screws telescope in the bone plate. These designs do inhibit rotation of the head fragment, but are large in size.

SUMMARY OF THE INVENTION

Therefore, it is an object of the present invention to provide a screw assembly which withstands torsional moments and which may be easily implanted also in patients with a small stature.

This object is achieved by a screw assembly according to claim 1. The inventive bone screw assembly for fixation into a bone comprises a first bone screw element with an elongated body including a threaded first end with a first external screw thread and a second end. The first external screw thread has a first handedness and a first lead length. The first bone screw element further comprises an internal thread feature with a second handedness located within a bore or a central channel provided within said elongated body. The bone screw assembly additionally comprises a second bone screw element including at least one second external screw thread with the second handedness and a second lead length. Thereby, the second handedness is the opposite of said first handedness and/or said first lead length is different from said second lead length. The second bone screw element is arranged at least within said bore and said second external screw thread is engaged with said internal thread feature. The second bone screw element is movable from a first implantation configuration, where the second bone screw element is arranged completely at least within said bore and a second implantation configuration where the second bone screw element at least partially protrudes from said bore.

As the second external screw thread comprises a different handedness and/or a different lead length as the first external screw thread, once the second bone screw element is moved to the second implantation configuration the bone screw assembly will be secured against rotation caused by any torsional moment acting thereon. If both external screw threads have a different handedness, a rotational moment in one direction may cause either the first or the second bone screw element to turn, however this turning motion will be blocked by the other bone screw element, as the rotational moment is oriented into the a direction which prohibits a turning motion for this other bone screw element.

In the case where both external screw threads have a different lead length, a rotational moment may cause the bone screw assembly to slightly turn, however, as both bone screw elements travel a different distance per turn due to the differing lead lengths, the turning motion will be quickly stopped, since the screw threads of at least one of the two bone screw elements will abut the threads cut into the bone, hence leading to a frictional lock of the screw thread within the bone.

It has to be noted that in the case where a different handedness is used, the lead length of the first external screw thread and the second external screw thread may be the same.

While the use of either a different handedness or a different lead length of both external screw threads works to lock the bone screw assembly in a rotational manner within a bone a combination of both, i.e. provision of external screw threads having different handedness and different lead length may be used. This is expressed by the terminology "and/or" which signifies that either one of the two or both together may be used.

The elongated body of the first bone screw element is preferably cylindrical and has an overall length, i.e. a distance between the first and the second end of the elongated body which is dependent on the intended use of the bone screw assembly, the target bone or the size of the patient. The same applies to the diameter of the elongated body. In one embodiment of the present invention, the elongated body of the first bone screw element has a constant diameter along its entire length. However, preferably, the diameter of the elongated body of the first bone screw element may also vary.

In the present application "handedness" is understood as the direction in which the helix of the screw thread is winding around the central axis of a bone screw element. Two different states of handedness are possible: either "right handedness" or "left handedness". A bone screw element with a "right handed" screw thread will move away of a viewer when turned in a clockwise direction and move towards the viewer when turned in a counterclockwise direction. Accordingly, a "left handed" screw thread will exhibit the opposite behaviour.

An "external screw thread" as understood in the present invention is a screw thread which is arranged on an outside circumference of a bone screw element. Accordingly, an "internal screw thread" is understood as a screw thread which is arranged on an inside circumference, e.g. in a bore or internal channel of a bone screw element. An external screw thread may therefore by threadingly engaged with an internal screw thread if both have a matching handedness, lead number, lead length and pitch.

A "lead length" as understood in the present application is the distance along a screw axis that is covered by the same lead with a full 360° turn of the bone screw element.

The external as well as the internal screw threads used in the present invention may have only one lead start, i.e. only one single thread helix winding around the central axis of the bone screw element.

Preferably, the screw threads have two or more lead starts, i.e. two or more separate thread helices winding around the central axis of the bone screw element.

Preferably, the first bone screw element comprises a bore as well as a central channel located in the elongated body.

The bore and the central channel are preferably arranged concentric with the central axis of the elongated body. The diameter of both the bore and the central channel are smaller than the outside diameter of the elongated body and chosen such that the difference of diameter between the outside diameter of the elongated body and the diameter of the bore or central channel leaves a wall thickness for the elongated body having sufficient strength.

Both the bore and the central channel may have the same diameter. However, preferably, both the bore and the central channel have different diameters. Further preferably, the bore is in fluid communication with the central channel, i.e. bore and central channel form a common cannulation through the entire length of the elongated body from the first end to the second end. Preferably, both the bore and the central channel have a constant diameter along their respective lengths. Alternatively, the diameters of the bore and/or of the central channel may vary along their respective length. A suitable instrument to impart a turning motion to the second bone screw element may be inserted through the central channel as well as at least partially through the bore. Such an instrument may for example be a screw driver.

The internal thread feature is preferably provided on the inner circumference of said bore or on the inner circumference of said central channel. The internal thread feature has a second handedness and a second lead length.

The second bone screw element preferably comprises a second elongated cylindrical body on which the second external screw thread is provided. The second external screw thread preferably has the second handedness and the second lead length corresponding to the second handedness and the second lead length of said internal thread feature. The diameter of the second bone screw element further preferably is chosen such that the second bone screw element may be inserted at least into said bore and said second external screw thread may be threadingly engaged with said internal thread feature.

The first handedness is preferably the opposite of said second handedness, i.e. if the first handedness is a left handedness, the second handedness is a right handedness and vice versa. Alternatively, the first lead length differs from the second lead length. As a further preferred alternative, the first handedness may be the opposite of the second handedness and the first lead length may be different from the second lead length.

As a rule of thumb, it may be stated that the difference in lead length between the first external screw thread and the second external screw thread should be chosen as large as possible. Thereby, a different handedness of a lead may be expressed as negative value. E.g. when the lead length of the first external screw thread is 3 mm and the lead length of the second external screw thread is 6 mm the difference has a value of 3 mm. However, when the lead length of both external screw threads is 3 mm, but one of the leads has an opposite handedness, i.e. a value of −3 mm, the difference has a value of 6 mm. Preferably, the second bone screw element is arranged at least within said bore of said first bone screw element. Further preferably, the second bone screw element is arranged both within said bore and at least partially within said central channel. In the latter case, the diameter of the second bone screw element is chosen such that an insertion both into the bore and at least a part of the central channel is possible.

The first implantation configuration is the configuration used to implant the bone screw assembly into a bone. In this configuration, the second bone screw element is completely arranged at least within said bore, i.e. the second bone screw element and thus the second external thread feature arranged thereon does not protrude from said first bone screw element. The bone screw assembly may therefore be screwed into e.g. a pre-drilled blind hole in a bone. Once the bone screw assembly is in place, the second bone screw element is turned, e.g. by means of an instrument inserted through the central channel from the second end, such that the second bone screw element is advanced into the bone by linearly moving out of the threaded first end of said first bone screw element. Since a turning motion is needed for advancement of the second bone screw element due to the engagement of the second external screw thread with the internal thread feature, the second bone screw element will be screwed into the bone as well.

In the second implantation configuration, the second bone screw element protrudes at least partially from the first bone screw element, i.e. it has been advanced over a certain distance. However, such as the anti-rotational effect is achieved, the second external screw thread needs to be still engaged at least partially with the internal thread feature. The second bone screw element therefore needs to be advanced enough to be tightly screwed into the bone while still being partially engaged with the internal thread feature.

Preferably said threaded first end has a first length extending towards the second end of the elongated body and terminating at a transition region. The bore is located within the elongated body in the area of said threaded first end. The central channel extends within the remaining portion of the elongated body from said transition region to said second end. The bore and the central channel are in fluid communication at the transition region. The internal thread feature is arranged in said central channel and extends from the transition region towards said second end.

The transition region marks the transition from the threaded first end to the remaining portion of the elongated body of the first screw element. Said remaining portion preferably comprises no screw thread and may be configured to interact with other implant parts, such as a plate, intramedullary nail or the like.

The threaded first end preferably has a larger diameter than the remaining portion of the elongated body. Hence, the transition region comprises a slope on its outer circumference which allows a change of the outside diameter of the elongated body. Said slope may have any suitable inclination angle.

Preferably, the bore has a larger diameter than said central channel and the second bone screw element includes a threaded head portion and a threaded tail portion. The diameter of the threaded head portion is larger than the diameter of the threaded tail portion and the diameter of the threaded head portion is smaller than the diameter of said bore but larger than the diameter of said central channel, wherein said second external screw thread is located on said threaded tail portion.

In this preferred configuration, the second external screw thread on the tail portion interacts with the internal thread feature located within the central channel. When advancing the second bone screw element from the first implantation configuration to the second implantation configuration, the threaded head portion may engage with the bone by means of its portion of external screw thread.

Hence, different portions of an external screw thread are used to secure the second bone screw element into the bone and to the internal thread feature. This allows e.g. the use of different diameters of the external screw thread in both portions.

Preferably, the threaded head portion comprises a thread with the same handedness and lead length as the second external screw thread. Hence, a turning motion of the second bone screw element used to advance the second bone screw element from the first implantation configuration to the second implantation configuration allows the threaded first end to be screwed into the bone.

Further preferably, the first handedness is opposite of the second handedness. This allows a very efficient securement of the bone screw assembly against rotational moments.

Preferably, the first external screw thread has a lead length which is preferably at least twice the lead length of said second external screw thread or vice versa. With this configuration, an efficient securement of the bone screw assembly against rotational moments may be achieved.

Alternatively, the bone screw assembly further comprises a third bone screw element with at least one third screw thread having the second handedness or the second lead length, wherein the internal thread feature is located within the central channel and extends up to the second end of the elongated body.

With this configuration, the third bone screw element may be secured to the first bone screw element at the second end by means of interaction of the third screw thread with the internal thread feature. This allows using the inventive bone screw assembly to secure two bone fragments together, while the bone screw assembly is secured against any rotational momentum in both bone fragments.

The third bone screw element may have a constant diameter, but preferably comprises a body having two different diameters. One diameter is chosen such that the third screw thread arranged thereon may be engaged with the internal thread feature, while the other diameter may be chosen to equal the diameter of the remaining portion of the second bone screw element. Alternatively, the other diameter may be chosen such as to be equal to the diameter of the threaded first end of the first bone screw element.

In an alternative embodiment, the internal thread feature is located within the bore. In this case the second bone screw element is completely arranged within the bore in the first implantation configuration without that any part is arranged within the central channel. The entire second external screw thread is thereby used to interact with the internal thread feature in the first implantation configuration. In the second implantation configuration, a part of the second external screw thread is engaged into the bone, while a second part is still engaged with the internal thread feature.

Another object of the present invention relates to a bone fixation assembly comprising an inventive bone screw assembly and a bone plate. The bone plate includes a first substantially flat plate portion and a tube shaped protrusion which extends from the plate portion under an angle. The tube shaped protrusion is configured to slidingly receive the bone screw assembly.

Such a bone fixation assembly may primarily be used for the treatment of femoral neck fractures. As the inventive bone fixation assembly is secured against any movement caused by torsional moments, no further anti-rotation means must be foreseen, such that the bone fixation assembly has a reduced size. Hence, the inventive bone fixation assembly is perfectly suitable for implantation in small stature patients. Further, as only one screw assembly has to be implanted in the femoral head, the complexity of the necessary surgery is greatly reduced.

Preferably, the tube shaped protrusion comprises at least one anti-rotation means on its inner circumference and the first bone screw element includes a complementary anti-rotation means.

This allows a rotational locking of the screw assembly with the bone plate. The anti-rotation means may for example be provided in the form of a protrusion which may be engaged into a corresponding notch on the first bone screw element or vice versa. Preferably, more than one anti-rotation means may be provided. Alternatively, the bone screw assembly may be rotationally fixed to the bone plate by means of a screw, like a set screw.

Further preferred embodiments and combinations of features may be derived from the following detail description and the claims.

BRIEF DESCRIPTION OF THE DRAWINGS

The drawings used to explain the embodiments show.

Identical features are identified by the same reference signs throughout the figures.

PREFERRED EMBODIMENTS

Figure 1:
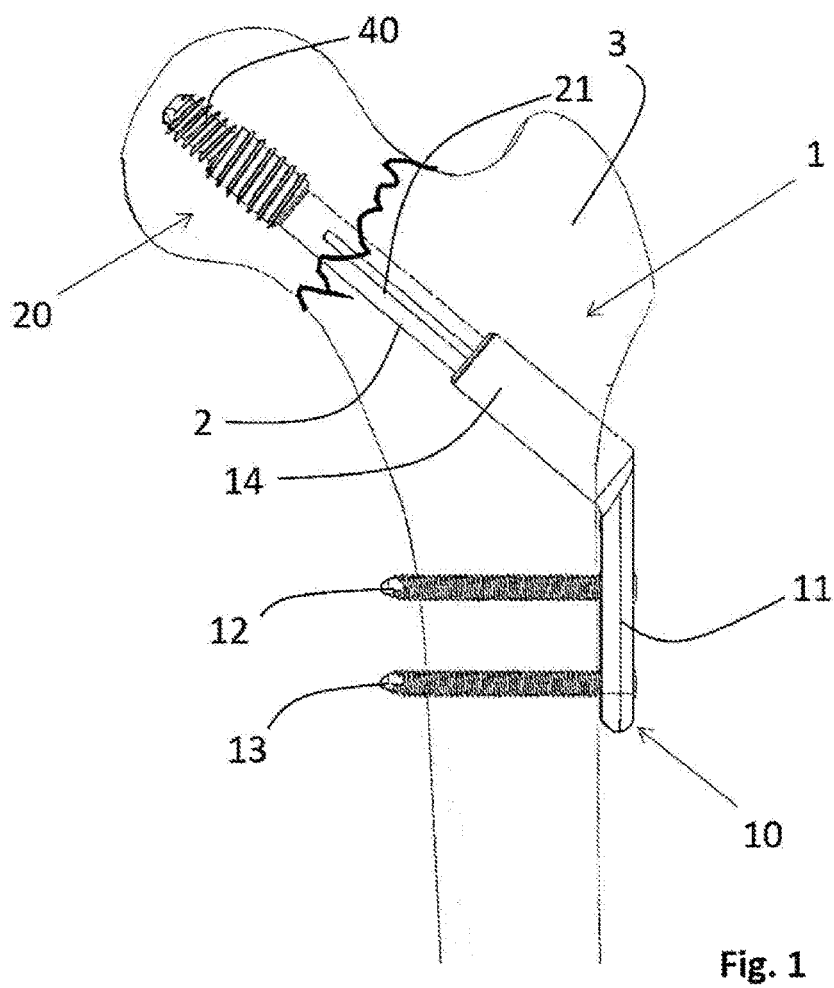
FIG. 1 a side view of the bone fixation assembly, comprising a bone plate and a bone screw assembly inside a femoral bone with a femoral neck fracture.

In reference to FIG. 1 a first embodiment of a bone fixation assembly 1 is shown, bridging a femoral neck fracture. The bone fixation assembly comprises a bone plate 10, a first bone fastener 12 and a second bone fastener 13 and a bone screw assembly 20. The bone plate 10 is attached to the lateral side of femoral shaft 3. The bone screw assembly 20 extends from the bone plate 10 through the femur into the femoral head fragment 2. By bridging the fracture area 4, the bone screw assembly fixates the femoral head fragment 2 to the femoral shaft 3.

The bone screw assembly 20 consist of a first bone screw element 21 and a second bone screw element 40, as explained in greater detail below. The bone screw assembly 20 is slidingly engaged into the bone plate 10.

Figure 2:
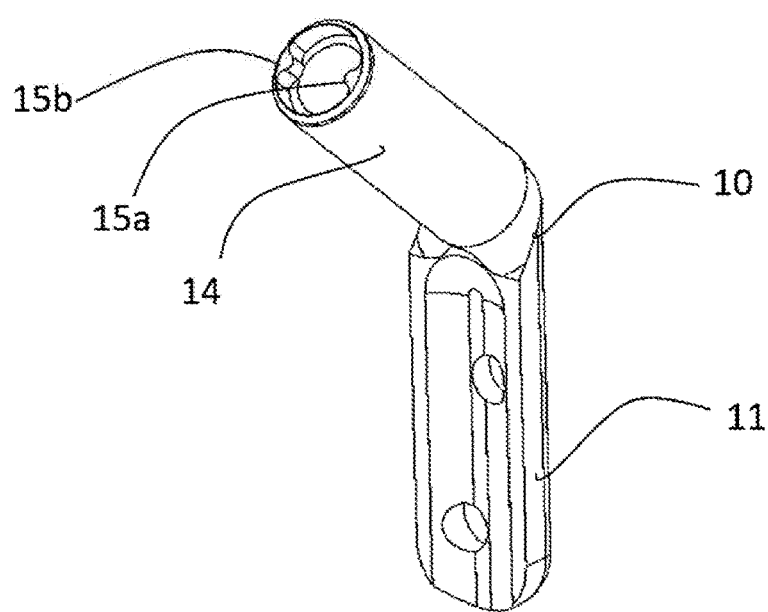
FIG. 2 details of the bone plate.

FIG. 2 shows the bone plate 10. The bone plate 10 comprises a first, flat plate portion 11 for fixation against a femoral bone by using a first bone fastener 12 and a second bone fastener 13. The number of bone fasteners depends on the fracture level and the plate size, and is at least one. Furthermore the bone plate 10 comprises a tube shaped protrusion 14, extending from the flat plate portion 11 under an angle of approximately 130°-140°. The tube shaped protrusion 14 is intended for countersunk placement inside a bone, as illustrated in FIG. 1. The tube shaped protrusion 14 is configured to receive the bone screw assembly 20, wherein said bone screw assembly 20 is slidingly and rotationally engaged inside the tube shaped protrusion 14.

For rotational stability the tube shaped protrusion 14 comprises at least one, preferably two or more male anti-rotation means 15a and 15b, which are evenly divided over the inner circumference of the tube shaped protrusion 14. The male anti-rotation means 15a extend from the inner wall of the tube shaped protrusion 14. Alternatively, the male anti-rotation means 15a may be configured as flat faces or as grooves.

The first male anti-rotation means 15a and the second male anti-rotation means 15b are configured to cooperate with complementary female anti-rotation means arranged on said bone screw assembly 20, wherein the cooperating sets of anti-rotation means inhibit rotation of the first bone screw element 21 of the bone screw assembly 20 in relation to the bone plate 10.

Figure 3A:
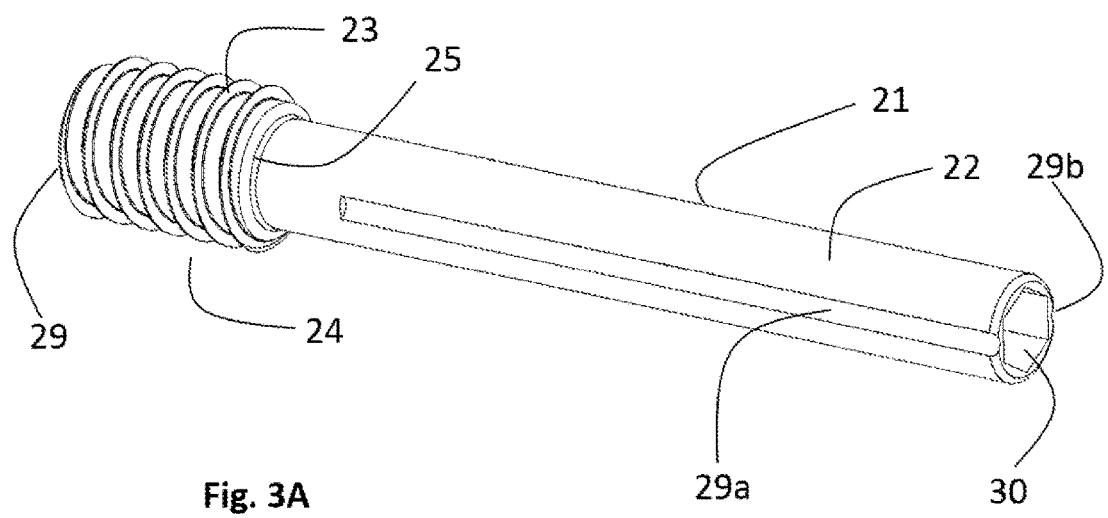
FIGS. 3A, 3B a first embodiment of the first bone screw element.
Figure 3B:
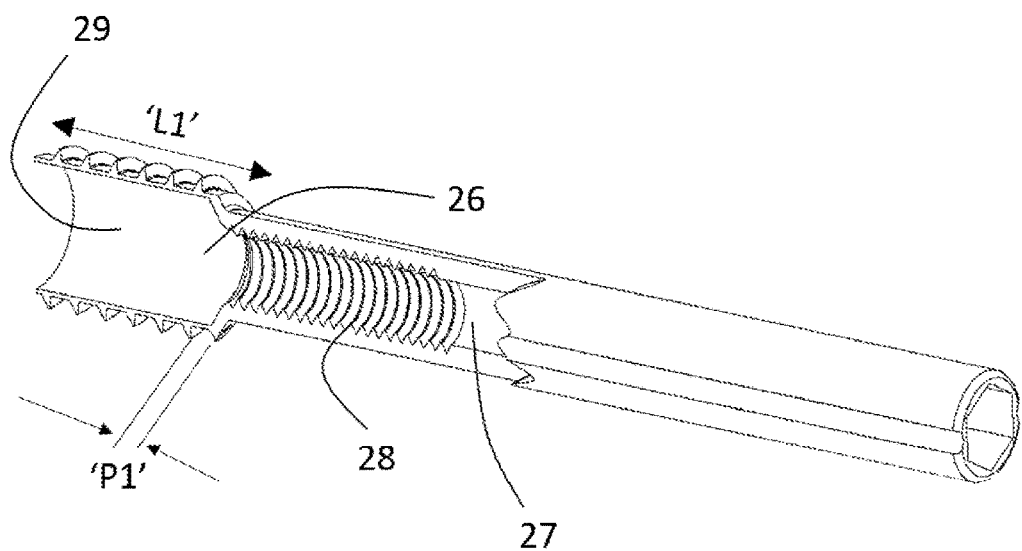

FIGS. 3A and 3B show the individual elements of the first bone screw element 21. The first bone screw element 21 comprises a first elongated cylindrical body 22, which extends from a first end 29 to a second end. The first elongated cylindrical body 22 comprises a head portion with a first external screw thread 23 for fixation in the target bone, forming the threaded first end 24. In a preferred embodiment, the first external screw thread 23 is of right handedness. The pitch 'P1' of said first external screw thread 23 is 1.0 mm or larger, preferably at least 2.5 mm.

A large portion of the first elongated cylindrical body 22 is of smaller diameter than the threaded first end 24. A first stepped transition region 25 is arranged between the threaded first end 24 and the remaining portion of the elongated cylindrical body 22. The stepped transition is located at a distance 'L1' of approximately 15 mm from the first end 29 of the first bone screw element, wherein distance 'L1' can vary from 10 to 30 mm, depending on overall length of the bone screw assembly 20. The required overall length of the bone screw assembly is related to the size of the target bone and patient.

The threaded first end 24 furthermore comprises a bore 26 extending approximately to the transition region 25.

A central channel 27 extends from the transition region 25 to the second end of the first bone screw element 21, wherein the diameter of the central channel 27 is substantially smaller than the diameter of the bore 26. The central channel 27 is configured to receive a screwdriver, as explained in greater detail below. Starting from the intersection of the central channel 27 and the bore 26 in the transition region 25, the central channel 27 comprises an internal thread feature 28. In a preferred embodiment the internal thread feature 28 is of left handedness and has a lead with two or more lead-starts. Furthermore the internal thread feature 28 has a lead of substantially equal length compared to the threaded head portion 44 of the second bone screw element 40, as described for FIGS. 4A and 4B below.

Further, the first elongated cylindrical body 22 comprises at least one, preferably two or more female anti-rotation means 29a, 29b, which are evenly divided over the circumference of the elongated shaft. The female anti-rotation means 29a, 29b are configured as grooves extending along the elongated shaft. Alternatively the female anti-rotation means 29a, 29b may be configured as flat faces or even as long protrusions extending from the elongated shaft. The female anti-rotation means 29a and 29b are configured to cooperate with the complementary male anti-rotation means 15a, 15b of the bone plate 10, wherein the cooperating sets of anti-rotation means 15a, 15b, 29a, 29b inhibit rotation of the first bone screw element 21 in relation to the bone plate 10.

At the second end, the first bone screw element 21 comprises a first drive 30. The first drive 30 is configured to engage with a screw-driver.

Figure 4A:
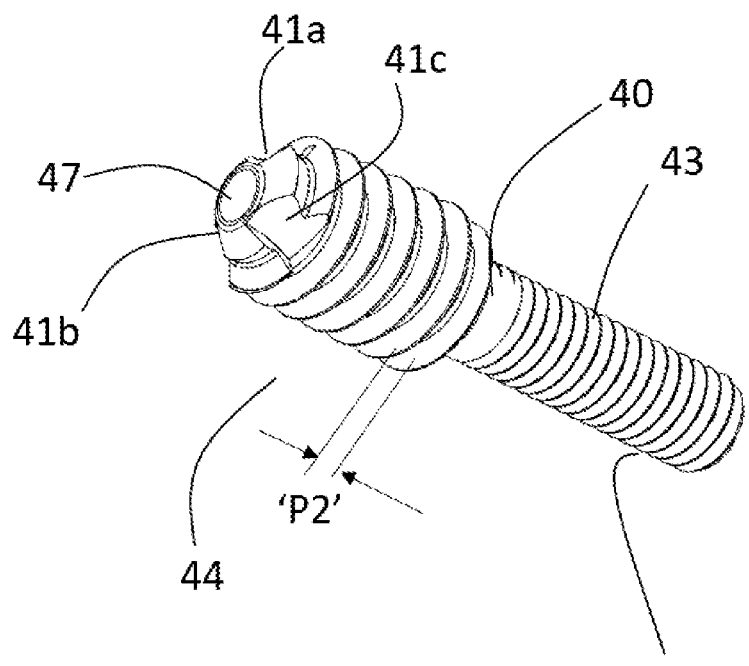
FIGS. 4A, 4B a first embodiment of the second bone screw element.
Figure 4B:
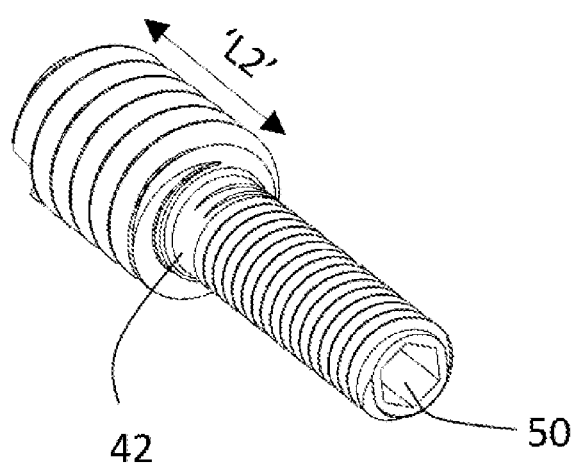

Referring to FIGS. 4A and 4B, the second bone screw element 40 is shown in detail. The second bone screw element 40 comprises a second cylindrical body 42, extending from a first end to a second end and comprising two outer diameters. The second cylindrical body 42 comprises a threaded head portion for fixation in the target bone comprising a first part of a second external screw thread 44 and a threaded tail portion for engagement into the first bone screw element 21 comprising a second part of the second external screw thread 46. In a preferred embodiment, the first part of the second external screw thread 44 is of left handedness. The pitch 'P2' of the first part of the second external screw thread 44 is 1.0 mm or larger, preferably at least 2.0 mm.

A large portion of the second cylindrical body 42 is of smaller diameter than the threaded head portion, forming a second stepped transition region. The second stepped transition region is located at a distance 'L1' of approximately 15 mm from the tip of the second bone screw element 40, wherein the distance 'L1' can vary from 10 to 30 mm, depending on the overall length of the bone screw assembly 20. The second threaded head portion comprises the tip with cutting edges 41a, 41b, 41c. The cutting edges 41a, 41b, 41c are configured to cut threads into the femoral head fragment 2.

In a preferred embodiment the second part of the second external screw thread 46 is of left handedness and has a lead with two or more lead-starts. The second part of the second external screw thread 46 corresponds in lead length, pitch and shape to the internal thread feature 28 of the first bone screw element 21.

In addition, a central cannulation 47 extends from the first end to the second end of the second bone screw element 40. The cannulation 47 is configured to receive a K-wire or guide wire for guided implantation.

At the second end, the second bone screw element 40 comprises a second drive 50. The second drive 50 is configured to engage with a screw-driver.

Figures 5A, 5B:
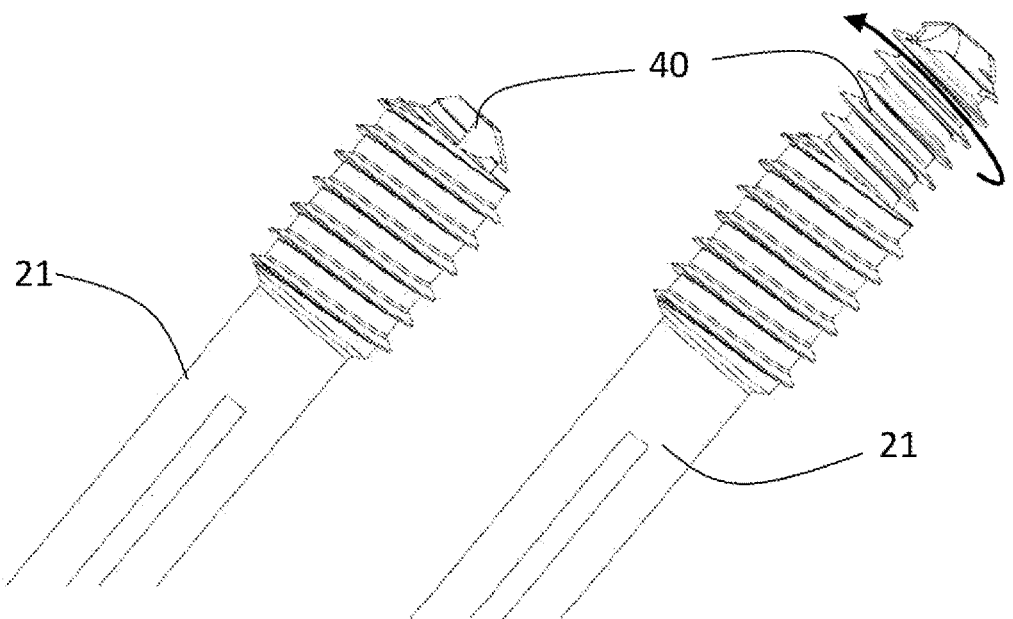
FIG. 5A-5D a bone screw assembly with the first bone screw element according to FIG. 3 and the second bone screw element according to FIG. 4 in the first and the second implantation configuration.
Figures 5C, 5D:
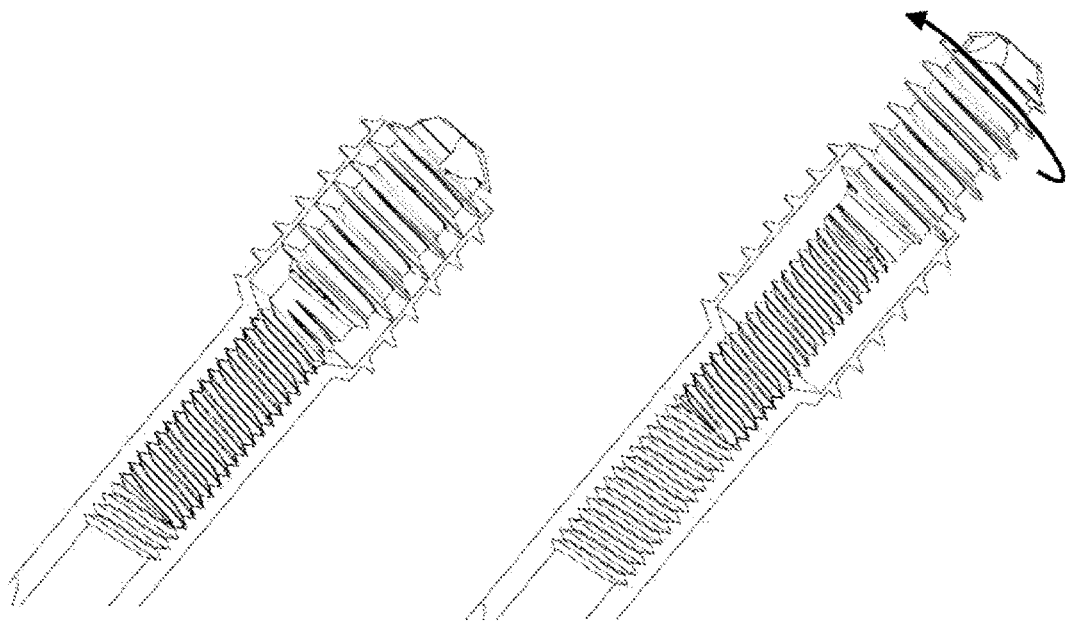

FIGS. 5A-5D shows the interaction between the first bone screw element 21 and the second bone screw element 40. FIGS. 5A and 5B show the bone screw assembly 20 in a first implantation configuration and a second implantation configuration. FIGS. 5C and 5D illustrate the first and second implantation configurations in a partial cross-sectional view. By counter clockwise rotation of the second bone screw element 40 relative to the first bone screw element 21, the second bone screw element 40 is advanced forward and will at least partially protrude out of the first bone screw element 21. To initiate the rotation, a screwdriver is engaged into drive 50 of the second bone screw element 40.

In an alternative embodiment of the bone screw assembly 20, a further element, such as a countering bolt, is engaged in internal thread feature 28. Upon tightening of the countering bolt against the second bone screw element 40, the second bone screw element 40 is locked inside the first bone screw element 21 in a play-free manner.

Figures 6A, 6B:
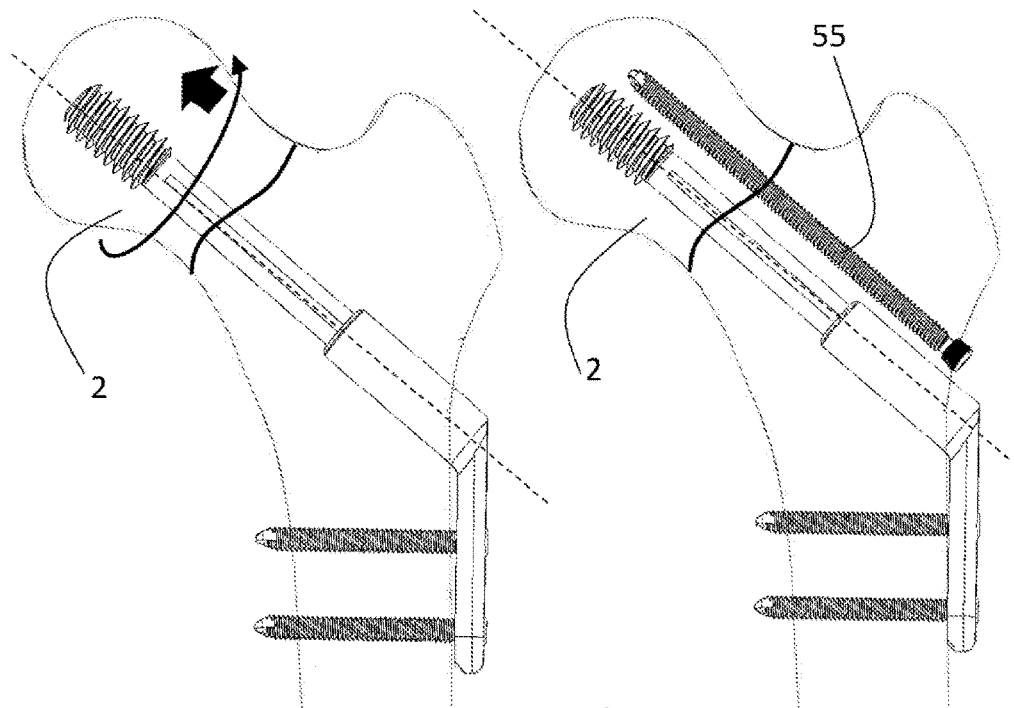
FIG. 6A-6C the mechanical principle that prevents rotation of the femoral head using the bone screw assembly according to FIG. 5 in comparison with a femoral neck implant according to the prior art.
Figure 6C:
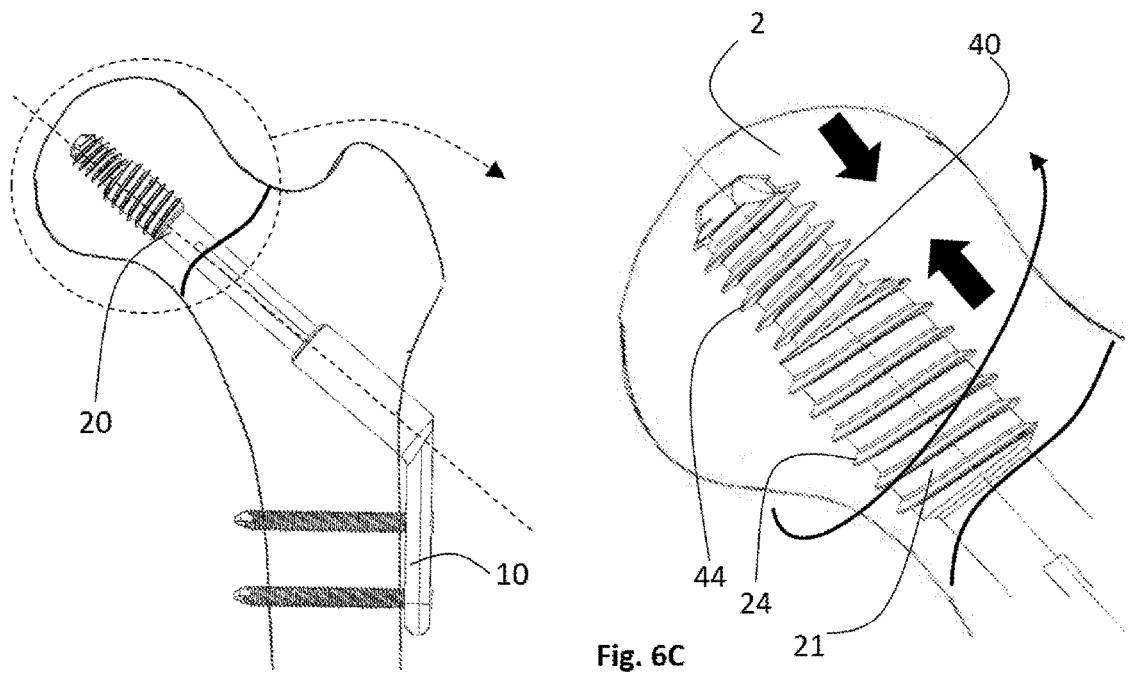

FIGS. 6A-6C show the principle with which the inventive bone screw assembly 20 withstands rotational moments compared to the prior art fixation.

As illustrated in FIG. 6A, with conventional sliding hip screw systems, torsional moments and loads exerted to the head-fragment 2 could cause the head-fragment 2 to rotate. Upon rotation, the head-fragment 2 translates parallel to the screw shaft. Clinically, rotation of the head-fragment 2 would cause loss of the fracture reduction. Normally for biomechanical reasons, the central hip screw is placed in the lower third of the femoral neck. Loss of reduction and turning of the head-fragment 2 could potentially damage the blood supply to the head-fragment 2, leading to avascular necrosis of the head-fragment 2. Currently, only by insertion of a second anti-rotation screw 55 as shown in FIG. 6B, the femoral head-fragment 2 is stabilised against rotational moments. The disadvantage of the extra screw is that the necessary bone stock must be available. Especially in small stature patients the femoral neck can be too small for two fixation components.

FIG. 6C shows the fixation principle of the inventive bone screw assembly 20. The head-fragment 2 engages with the two screw threads with opposite handedness of the threaded first end 24 of first screw element 21 and the threaded head portion of the second screw element 40. The screw assembly 20 furthermore is rotationally blocked into the bone plate 10 by the cooperating anti-rotation means of the screw-assembly 20 and the bone plate 10.

Rotational moments exerted to the head-fragment 2 would theoretically cause the head to rotate. Now, due to the opposite handedness of the first external screw thread 23 and the second external screw thread 44, a rotational moment would initiate the head-fragment 2 to translate in one direction on the first bone screw element 21 with a first handedness, and to translate in an opposite direction on the second bone screw element 40 with opposite handedness. As a result, due to the positive form-fit of left and right handed screw thread profiles, the head fragment is prevented from rotation.

Figure 7:
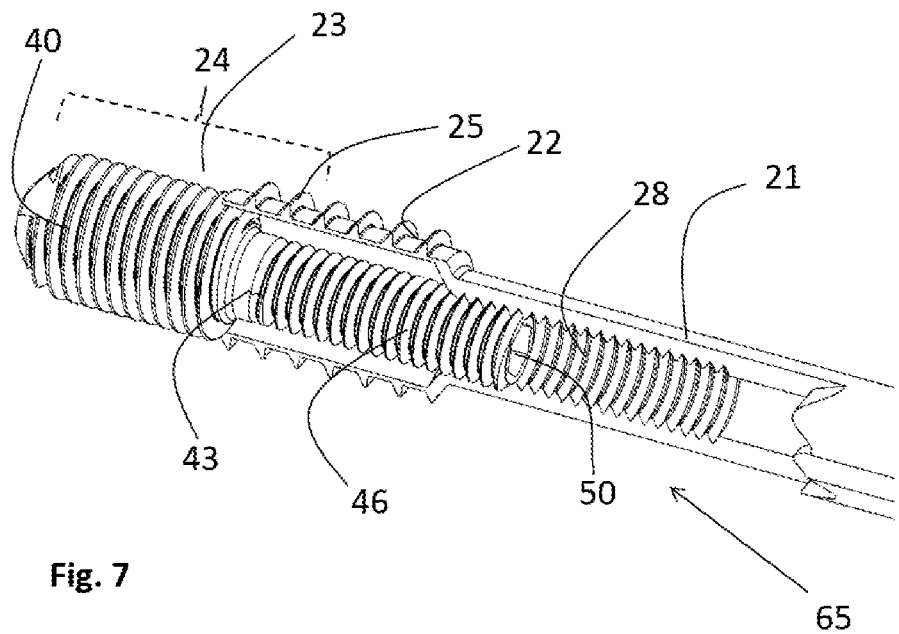
FIG. 7 a second embodiment of a bone screw assembly where both bone screw elements have the same handedness but different lead lengths.

FIG. 7 shows another alternative embodiment for the bone screw assembly 65 in a partially cross-sectional view. The third alternative bone screw assembly 65 is substantially similar to the bone screw assembly 20. The first bone screw element 21 and the second bone screw element 40 have the same handedness but differ significantly in lead length. Upon rotation, a bone would tend to translate faster on the first bone screw element 21 compared to the second bone screw element 40. As a result, due to the positive form-fit of the screw thread profiles with different lead length, the bone screw assembly 20 is prevented from rotation within the bone.

Figure 8:
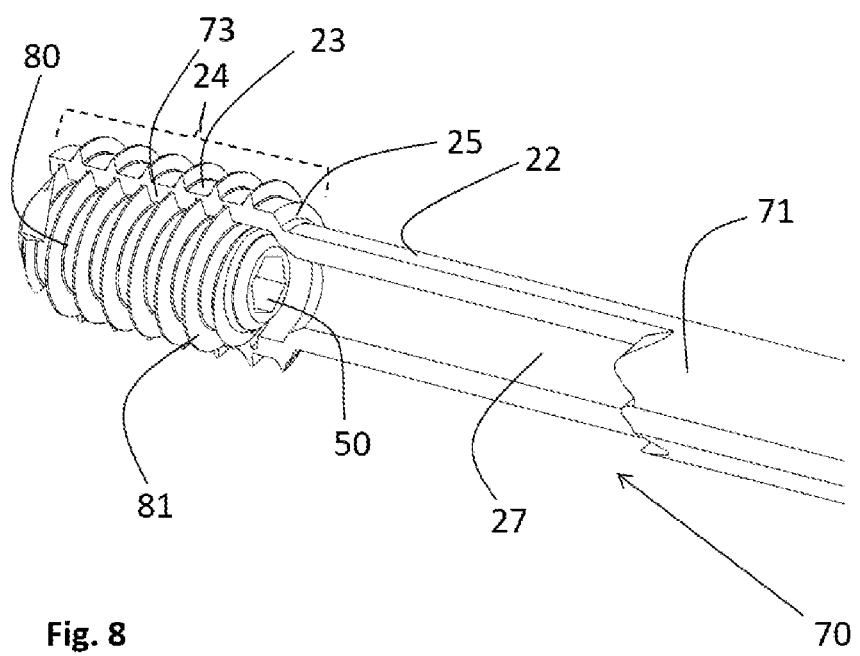
FIG. 8 a third embodiment of a bone screw assembly.

FIG. 8 shows another alternative embodiment of a bone screw assembly 70 in a partially cross-sectional view. The bone screw assembly 70 is substantially similar to the bone screw assembly 20. The bone screw assembly 70 comprises a first bone screw element 71 comprising all embodiments as described for the first bone screw element 21, except for the internal thread feature 28. The internal thread feature 73 alternatively is located inside the bore 26.

The internal thread feature 73 is configured to threadingly engage with the second external screw thread 81 of the second bone screw element 80. In a preferred embodiment the internal thread feature 73 is of left handedness. Furthermore the internal thread feature 73 has a lead, pitch and shape of substantially equal length as the second external screw thread 81 of the second bone screw element 80.

FIGS. 9A to 9G show the implantation steps of the bone fixation assembly 1 in a bone.

Figures 9A, 9B:
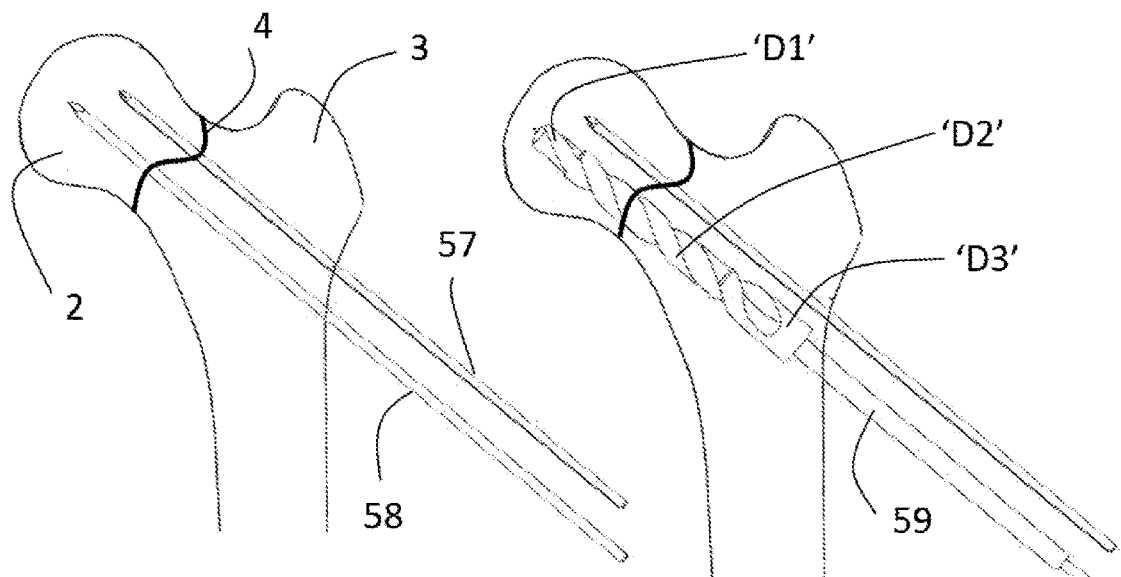
FIG. 9A-9G surgical steps for the implantation of the bone fixation assembly according to FIG. 1.

FIG. 9A shows the bony anatomy of a target bone, specifically the proximal femur 113 with a fracture area 4 and femoral head-fragment 2. The fracture area 4 is reduced and fixated by the insertion of at least one guide wire 57. A central guide wire 58 defines the intended position of the screw assembly 20.

FIG. 9B shows the pre-drilling of a hole extending from the lateral cortex of the proximal femur 113 into the head-fragment 2. A cannulated stepped drill 59 which comprises three drilling diameters is inserted over the central guide wire 58. The most distal drill diameter 'D1' corresponds to the core diameter of the threaded head portion 44 of the second bone screw 40. The second drill diameter 'D2' corresponds to the core diameter of the threaded distal end 24 of first bone screw element 21. The third drill diameter 'D3' corresponds to the outer diameter of the tube shaped protrusion 14 of the bone plate 10.

Figure 9C:
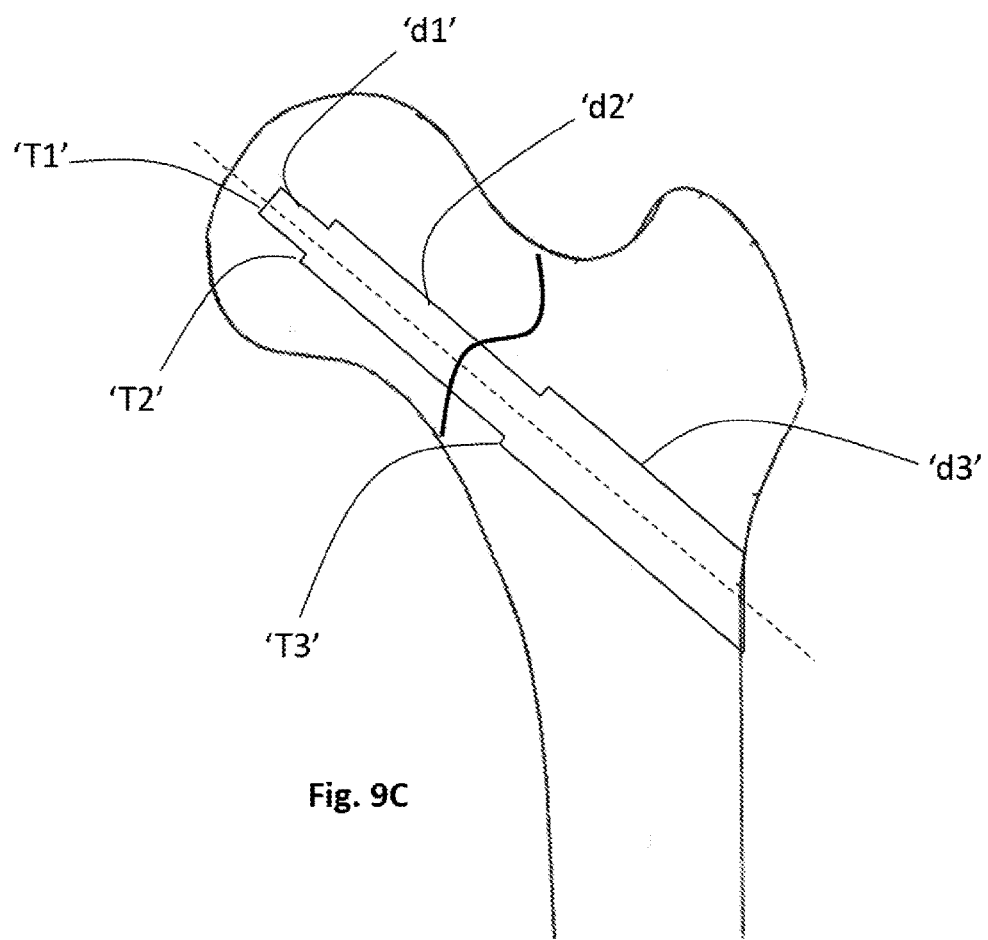

After drilling, as shown in FIG. 9C, the stepped bore in the proximal femur 113 comprises 3 bore transitions:

a first bore transition 'T1' at the most distal end of the bore between undrilled bone and the bore portion with bore diameter 'd1', wherein bore diameter 'd1' corresponds to the first drill-diameter 'D1', a second bore transition 'T2' located between bore diameter 'd1' and bore diameter 'd2', wherein bore diameter 'd2' corresponds to the second drill-diameter 'D2', and a third bore transition 'T3' located between bore diameter 'd2' and bore diameter 'd3', wherein bore diameter 'd3' corresponds to the third drill-diameter 'D3'.

Figure 9D:
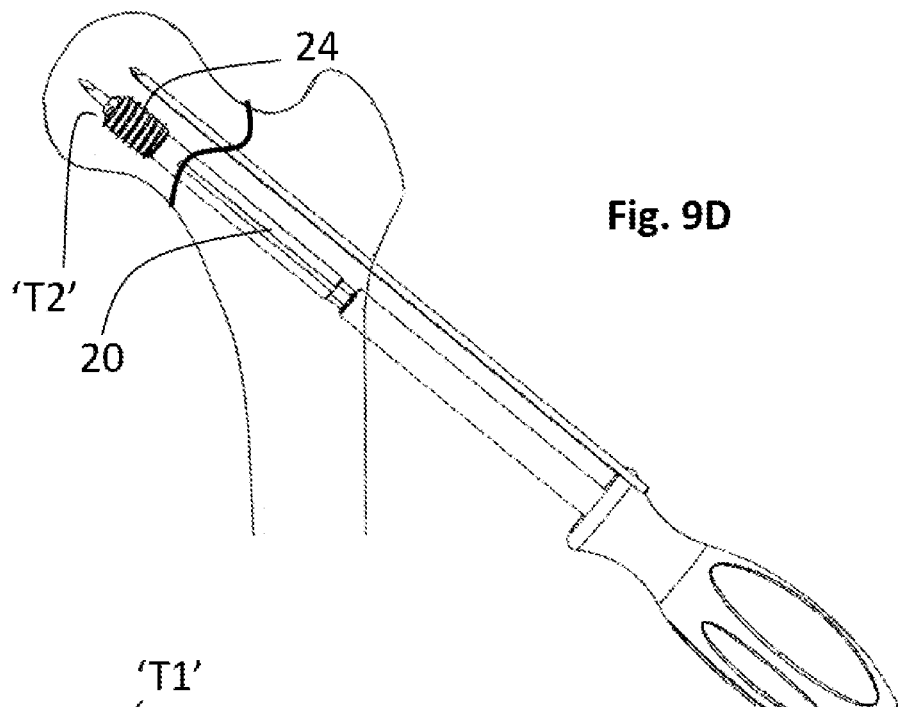

Referring to FIG. 9D, the bone screw assembly 20 is inserted into the proximal femur 113 over the central guide wire 58. The bone screw assembly 20 is inserted by right hand turning, until the distal threaded end 24 engages in the femoral head fragment 56, and abuts against the bore transition 'T2'.

Figure 9E:
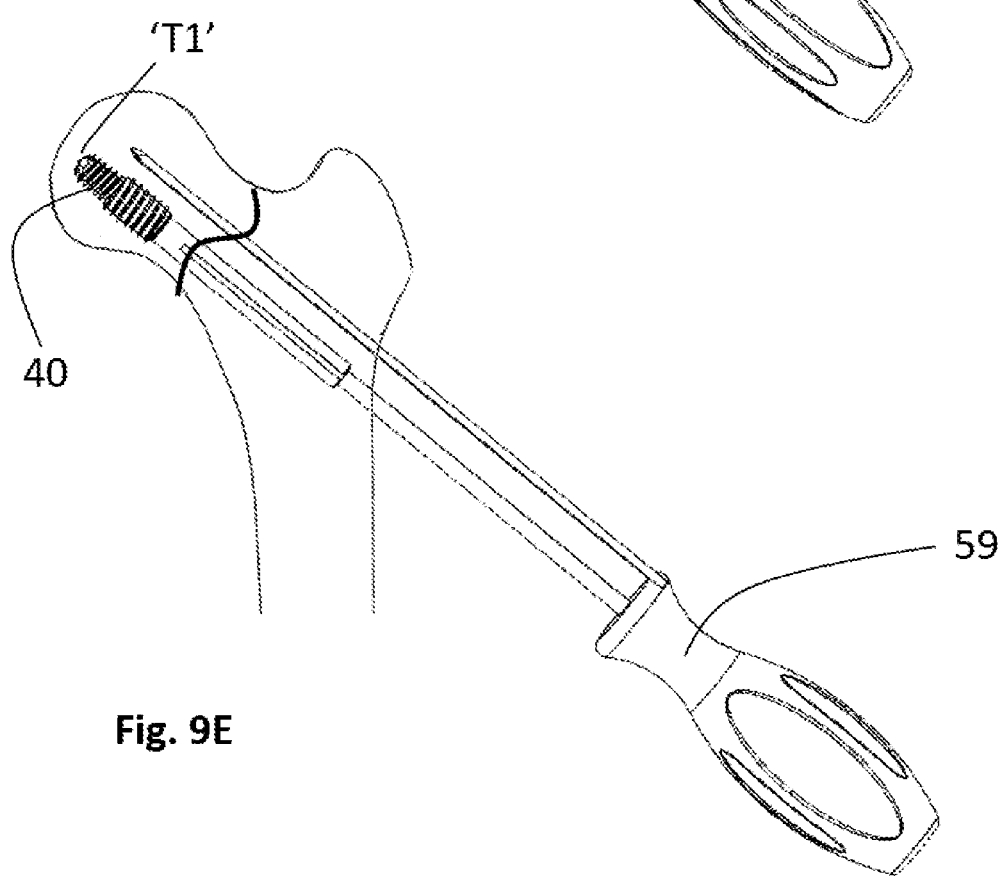

In a next step, as shown in FIG. 9E, a screw-driver 59 is inserted into the bone screw assembly 20 and engages into the drive 50 of the second bone screw element 40.

Upon counter clockwise turning of the screw-driver 59, the second bone screw element 40 will rotate and subsequently translate into the femoral head, until the tip of the second bone screw element 40 abuts with the end of the bore at bore transition 'T1'.

The head fragment 2 is fixated to the bone screw assembly 20 by two screw threads with opposite handedness, resulting in a fixation means withstanding rotational moments, axial tensile forces and axial compression forces, as described earlier in relation to FIG. 6C.

Figure 9F:
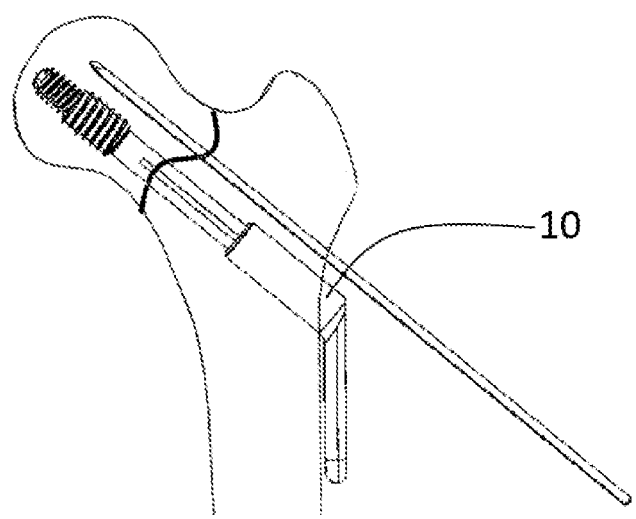

Referring to FIG. 9F, the bone plate 10 is slidingly engaged over the elongated shaft 22 of the first bone screw element 21. The female anti-rotation means 29a and 29b cooperate with the complementary male anti-rotation means 15a and 15b of the bone plate 10, wherein the anti-rotation means 15a, 15, 29a, 29b inhibit rotation of the first bone screw element 21 in relation to the bone plate 10.

Figure 9G:
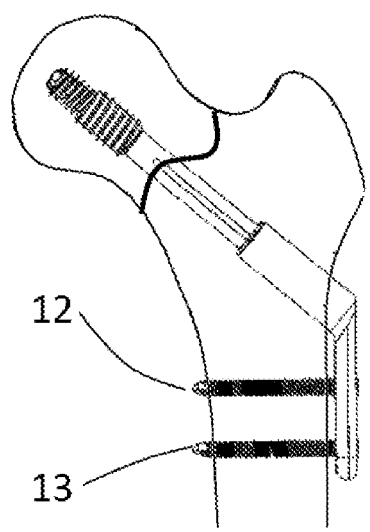

Referring to FIG. 9G, the insertion of bone fasteners 12 and 13 is shown. The head fragment 2 is rigidly fixated to the proximal femur 113.

Figure 10:
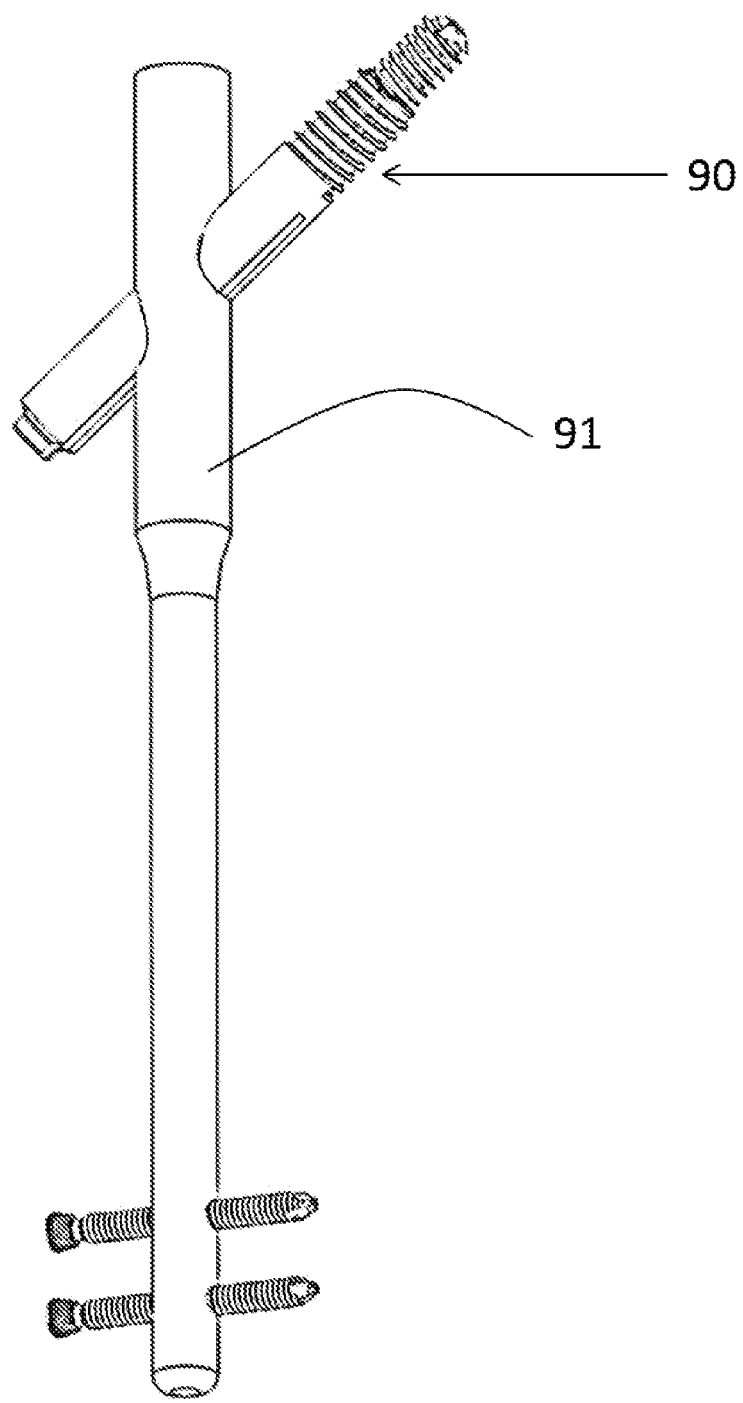
FIG. 10 a second embodiment of a bone fixation assembly wherein the bone screw assembly is part of an intramedullary nail.

FIG. 10 shows an alternative embodiment of a bone implant assembly. The screw assembly 90 is thereby engaged into an intramedullary nail 91.

Figure 11:
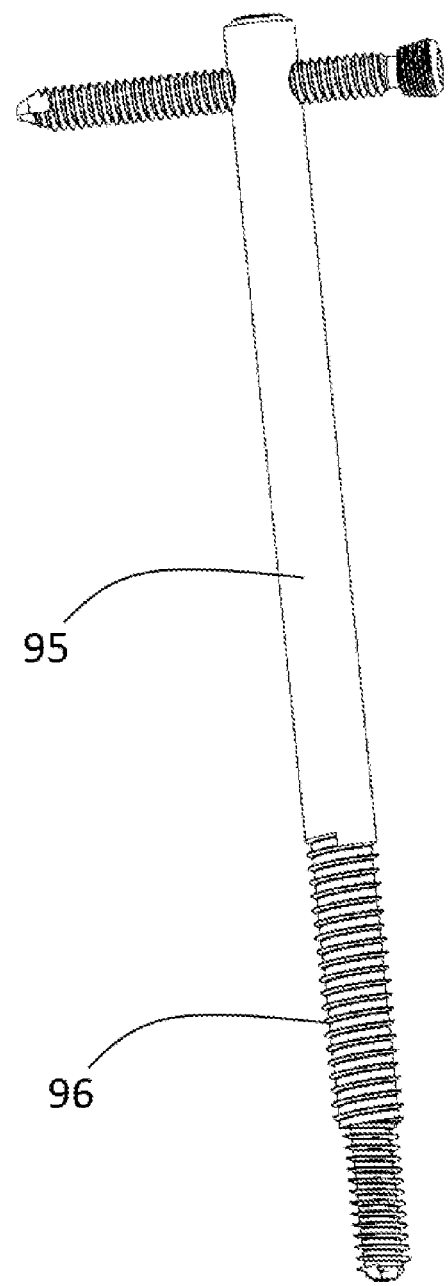
FIG. 11 a third embodiment of a bone fixation assembly wherein the bone screw assembly forms a part of a distal or proximal end of an intramedullary nail.

FIG. 11 shows another alternative embodiment of a bone implant assembly. In this embodiment, the bone fixation assembly 96 forms the distal or proximal end an intramedullary nail 95. The bone fixation assembly 96 thereby provides a full internal fixation into a target bone, at one end of the bone fixation assembly.

Figure 12A:
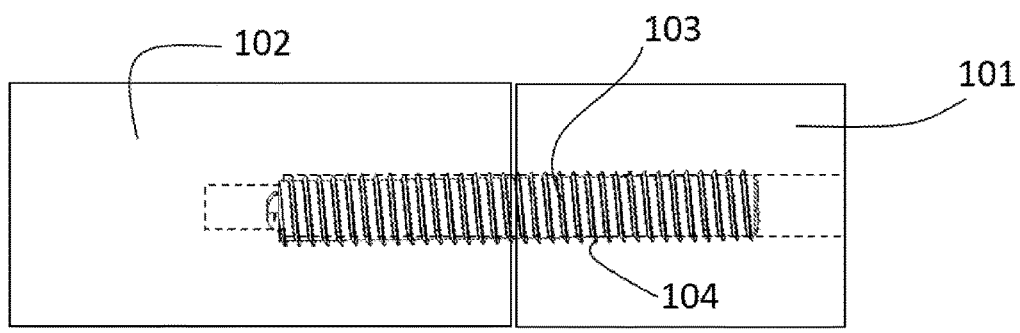
FIG. 12A-12E a fourth embodiment of a bone screw assembly with a third bone screw element.
Figure 12B:
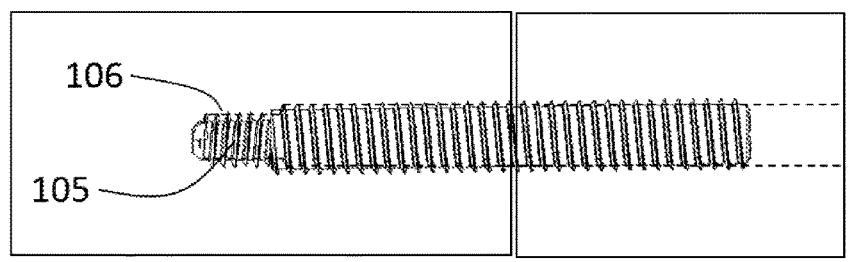
Figure 12C:
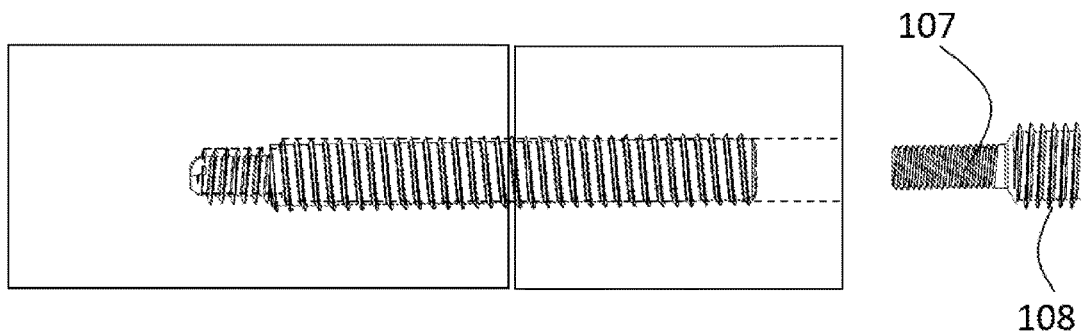
Figure 12D:
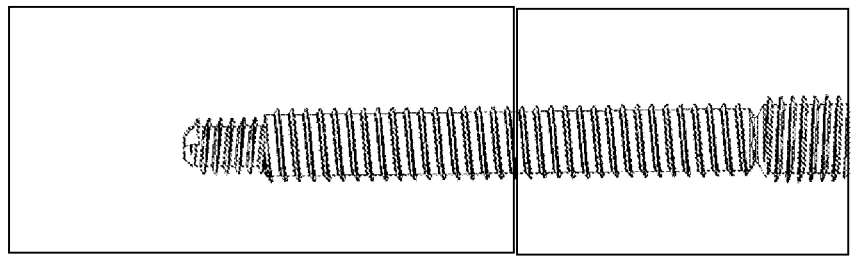

Referring to FIGS. 12A and 12B, another alternative embodiment of a bone screw assembly 100 is shown. The bone screw assembly 100 comprises three screw elements 103, 105, 107, of which two are of opposite handedness. The bone screw assembly 100 may be used for the fixation of a small bone fragment 101 against a main bone 102. The combination of the bone screw elements 103, 105, 107 with opposite handedness facilitates a fixation principle which may fixate the small bone fragment 101 and withstands rotational moments, tensional and compressional loads.

In detail, a first screw element 103 with a first external screw thread 104 with a first handedness is fixated in the small bone fragment 101 and the main bone 102. Then, a second bone screw element 105 having a second external screw thread 106 of a second handedness which is the opposite of the first handedness is advanced from the first bone screw element 103 into the main bone 102. Finally, a third screw element 107 is fixated in the small bone fragment 101 with a third external screw thread 108 of second handedness.

Figure 12E:
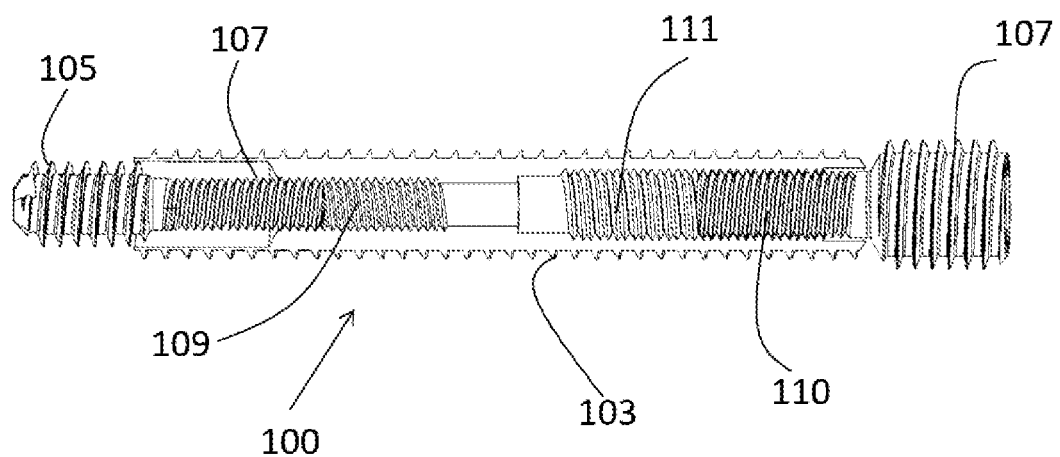

As illustrated in FIG. 12E, the first screw element 103 and the second screw element 105 are engaged by engagement of a third external screw thread 108 of second handedness located in a tail region of the second bone screw element 105 with an internal thread feature 109 of the first bone screw element 103. Furthermore, the second screw element 105 and the third screw element 107 are fixed together by means of an engagement of a fourth external screw thread 110 with a second internal thread feature 111, both of second handedness.

As a result, due to the opposite handedness of the bone engaging screw threads, a rotational moment would initiate the small bone fragment 101 to translate in one direction on the third bone screw element 107 and to translate in an opposite direction on the second bone screw element 105. As a result, due to the positive form-fit of left and right handed screw thread profiles, the bone screw assembly 100 is prevented from any rotation. The combination of the small bone fragment 101, the second bone screw element 105 and the third bone screw element 107 likewise prevents any rotation of the small bone fragment 101 relative to the bone screw assembly 100 by the same principle. Hence, this embodiment of the bone screw assembly 100 allows the fixation of a small bone fragment 101 with a main bone 100—or of any two bones—in a manner which is secured against rotational movement.

I claim:

1. A bone screw assembly for fixation into a target bone, comprising
   a) a first bone screw with an elongated body including a threaded first end with a first external screw thread having a first handedness and a second end, the first bone screw further comprising a bore, a central channel and an internal thread feature with a second handedness located within the bore or the central channel of the first bone screw and provided within said elongated body, the first bone screw being configured to be non-expandable during fixation into the target bone;
   b) a second bone screw comprising at least one second external screw thread with the second handedness,
   wherein said second handedness is the opposite of said first handedness, wherein said second bone screw is arranged at least within said bore, and said second external screw thread is engaged with said internal thread feature of the first bone screw, wherein the second bone screw is movable from a first implantation configuration where the second bone screw is arranged substantially completely within said bore, or said bore and central channel, and a second implantation configuration where the second bone screw protrudes from said bore such that the second bone screw has been advanced into the target bone from said bore more than in the first configuration while still being partially engaged with said internal thread feature, and wherein in the second implantation configuration, the first bone screw and the second bone screw are both arranged to be screwed in the target bone and threadedly directly engaged with the target bone to prevent the target bone from rotating with respect to the bone screw assembly.

2. The bone screw assembly according to claim 1, wherein said threaded first end has a first length extending towards the second end of the elongated body and terminating at a transition region, wherein the bore is located within said first end, wherein said central channel extends within the remaining portion of the elongated body from said transition region to said second end, said bore and said central channel being in fluid communication at the transition region, wherein said internal thread feature is arranged in said central channel and extends from the transition region towards said second end.

3. The bone screw assembly according to claim 2, wherein said bore has a larger diameter than said central channel, and said second bone screw includes a threaded head portion and a threaded tail portion, the diameter of the threaded head portion being larger than the diameter of the threaded tail portion, wherein the diameter of the threaded head portion is smaller than the diameter of said bore but larger than the diameter of said central channel and wherein said second external screw thread is located on said threaded tail portion.

4. The bone screw assembly according to claim 3, wherein said threaded head portion has a thread with the same handedness and lead length as the second external screw thread.

5. The bone screw assembly according to claim 1, wherein said first external screw thread and said internal thread feature have a first lead length, and said at least one second external screw thread has a second lead length, and wherein the first lead length is different from the second lead length.

6. The bone screw assembly according to claim 5, wherein the lead length of said first external screw thread is at least twice the lead length of said second external screw thread or vice versa.

7. The bone screw assembly according to claim 1, wherein the bone screw assembly further comprises a third bone screw with at least one third screw thread with the second handedness.

8. The bone screw assembly according to claim 1, wherein said internal thread feature is located within said bore.

9. A bone fixation assembly comprising a bone screw assembly according to claim 1.

10. The bone fixation assembly according to claim 9, wherein the bone fixation assembly further comprises a bone plate including a first substantially flat plate portion, wherein a tube shaped protrusion extends from the plate portion under an angle, said tube shaped protrusion being configured to slidingly receive the bone screw assembly.

11. The bone fixation assembly according to claim 10, wherein the tube shaped protrusion comprises at least one anti-rotation means on its inner circumference, and wherein the first bone screw comprises complementary anti-rotation means.

12. The bone fixation assembly according to claim 9, wherein the bone fixation assembly further comprises an intramedullary nail, wherein said bone screw assembly is engaged in said intramedullary nail.

13. The bone fixation assembly according to claim 9, wherein said bone screw assembly forms the distal or proximal end of an intramedullary nail.

14. A method of implanting the bone screw assembly of claim 1, the method comprising:
  screwing said first bone screw into the target bone by rotating it in a first direction;
  advancing said second bone screw-axially from said first bone screw so that said second bone screw protrudes from said first bone screw; and
  screwing said second bone screw into the target bone by rotating said second bone screw in a second direction, which is the opposite of the first direction.

* * * * *